US012657722B2

(12) United States Patent
Bennett et al.

(10) Patent No.: US 12,657,722 B2
(45) Date of Patent: Jun. 16, 2026

(54) SYSTEMS AND METHODS TO MAP AUTOREGULATION OF THE KIDNEY USING MAGNETIC RESONANCE IMAGING

(71) Applicant: Washington University, St. Louis, MO (US)

(72) Inventors: Kevin Bennett, St. Louis, MO (US); Edwin Baldelomar, St. Louis, MO (US)

(73) Assignee: Washington University, St. Louis, MO (US)

( * ) Notice: Subject to any disclaimer, the term of this patent is extended or adjusted under 35 U.S.C. 154(b) by 532 days.

(21) Appl. No.: 18/305,133

(22) Filed: Apr. 21, 2023

(65) Prior Publication Data

US 2023/0342936 A1 Oct. 26, 2023

Related U.S. Application Data

(60) Provisional application No. 63/333,899, filed on Apr. 22, 2022.

(51) Int. Cl.
G06T 7/00 (2017.01)
A61B 5/055 (2006.01)
(Continued)

(52) U.S. Cl.
CPC ............ G06T 7/0016 (2013.01); A61B 5/055 (2013.01); A61B 5/201 (2013.01); G16H 50/30 (2018.01);
(Continued)

(58) Field of Classification Search
CPC ...... G06T 7/0016; G16H 50/30; A61B 5/055; A61B 5/201
See application file for complete search history.

(56) References Cited

U.S. PATENT DOCUMENTS

| | | |
|---|---|---|
| 7,319,328 B1 | 1/2008 | Karmonik |
| 7,407,646 B2 | 8/2008 | Laurent |

(Continued)

FOREIGN PATENT DOCUMENTS

| | | | | |
|---|---|---|---|---|
| CN | 115282295 A | * | 11/2022 | ............. A61K 49/10 |
| WO | 2007059139 A2 | | 5/2007 | |

(Continued)

OTHER PUBLICATIONS

Beeman et al., Measuring Glomerular Number and Size in Perfused Kidneys Using MRI, Mar. 2011, Am J Physiol Renal Physiol 300: F1454-F1457, 2011 (Year: 2011).*

*Primary Examiner* — Wednel Cadeau
(74) *Attorney, Agent, or Firm* — Armstrong Teasdale LLP

(57) ABSTRACT

A method of mapping autoregulation of a kidney using magnetic resonance (MR) imaging is provided. The method includes acquiring a time series of MR images of a subject while the subject is at rest by acquiring MR images of an imaging region repeatedly over a period of time by applying a pulse sequence. The imaging region includes at least a kidney of the subject. The method also includes analyzing the time series of MR images along a temporal dimension, and identifying features associated with autoregulation of the kidney including tubuloglomerular feedback (TGF) in voxels of the MR images based on the analysis. The method further includes generating a map and/or a metric of the autoregulation based on the identified features, and outputting the map and/or the metric.

20 Claims, 15 Drawing Sheets
(10 of 15 Drawing Sheet(s) Filed in Color)

(51) Int. Cl.
    *A61B 5/20*         (2006.01)
    *G16H 50/30*       (2018.01)

(52) U.S. Cl.
    CPC ............... *G06T 2207/10016* (2013.01); *G06T 2207/10088* (2013.01); *G06T 2207/30084* (2013.01)

(56)                References Cited

U.S. PATENT DOCUMENTS

| | | | |
|---|---|---|---|
| 9,823,325 | B2 | 11/2017 | Bennett |
| 10,101,248 | B1 | 10/2018 | Campton |
| 10,251,592 | B2 | 4/2019 | Bennett |
| 10,835,159 | B2 | 11/2020 | Schabel |
| 11,238,975 | B2 | 2/2022 | El-Baz |
| 2008/0114235 | A1 | 5/2008 | Unal |
| 2008/0287815 | A1* | 11/2008 | Chon ................... A61B 5/0205 600/507 |
| 2009/0005693 | A1 | 1/2009 | Brauner |
| 2012/0000316 | A1 | 1/2012 | Heckmann |
| 2012/0003160 | A1* | 1/2012 | Wolf ................... A61B 5/0515 424/9.3 |
| 2014/0294734 | A1* | 10/2014 | Gulani ................... G01R 33/56 324/309 |

FOREIGN PATENT DOCUMENTS

| | | | |
|---|---|---|---|
| WO | 2014001961 | A1 | 1/2014 |
| WO | 2015054295 | A1 | 4/2015 |
| WO | 2020181051 | A1 | 9/2020 |

* cited by examiner

200 autoregulation mapping computing device

SYSTEMS AND METHODS TO MAP AUTOREGULATION OF THE KIDNEY USING MAGNETIC RESONANCE IMAGING

CROSS-REFERENCE TO RELATED APPLICATIONS

This patent application claims the benefit of U.S. Provisional Patent Application No. 63/333,899, filed on Apr. 22, 2022, titled "SYSTEMS AND METHODS TO MAP AUTOREGULATION OF THE KIDNEY USING MAGNETIC RESONANCE IMAGING," the entire contents and disclosures of which are hereby incorporated herein by reference in their entirety.

STATEMENT REGARDING G FEDERALLY SPONSORED RESEARCH & DEVELOPMENT

This invention was made with government support under DK020579 awarded by the National Institutes of Health. The government has certain rights in the invention.

BACKGROUND

The field of the disclosure relates generally to systems and methods of function mapping, and more particularly, to systems and methods of non-invasively mapping autoregulation of the kidney.

The kidney performs the function of blood filtration. Chronic kidney disease has been recognized as a leading public health problem worldwide. Further, diseases such as hypertension and diabetes negatively affect the functions of kidney. However, non-invasive early detection of kidney disease and kidney functions is currently unavailable.

BRIEF DESCRIPTION

In one aspect, a method of mapping autoregulation of a kidney using magnetic resonance (MR) imaging is provided. The method includes acquiring a time series of MR images of a subject while the subject is at rest by acquiring MR images of an imaging region repeatedly over a period of time by applying a pulse sequence. The imaging region includes at least a kidney of the subject. The method also includes analyzing the time series of MR images along a temporal dimension, and identifying features associated with autoregulation of the kidney including tubuloglomerular feedback (TGF) in voxels of the MR images based on the analysis. The method further includes generating a map and/or a metric of the autoregulation based on the identified features, and outputting the map and/or the metric.

In another aspect, a method of mapping autoregulation of a kidney using MR imaging is provided. The method includes receiving a time series of MR images of a subject while the subject is at rest. The time series of MR images were acquired by acquiring MR images of an imaging region repeatedly over a period of time, and the imaging region includes at least a kidney of the subject. The method also includes analyzing the time series of MR images along a temporal dimension, and identifying features associated with autoregulation of the kidney in voxels of the MR images based on the analysis. The method further includes generating a map and/or a metric of the autoregulation based on the identified features, and outputting the map and/or the metric.

In one more aspect, a method of mapping autoregulation of one or more organs outside a central nervous system of a subject using MR imaging, is provided. The method includes receiving a time series of MR images of a subject while the subject is at rest, wherein the time series of MR images were acquired by acquiring MR images of an imaging region repeatedly over a period of time, and the imaging region includes one or more organs outside a central nervous system of the subject. The method further includes analyzing the time series of MR images along a temporal dimension, and identifying features associated with autoregulation of the one or more organs in voxels of the MR images based on the analysis. The method also includes generating a map and/or a metric of the autoregulation based on the identified features, and outputting the map and/or the metric.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure will become better understood when the following detailed description is read with reference to the accompanying drawings in which like characters represent like parts throughout the drawings, wherein:

FIG. 8 depicts effects of time of repetition (TR) on aliasing.

Figure 1:
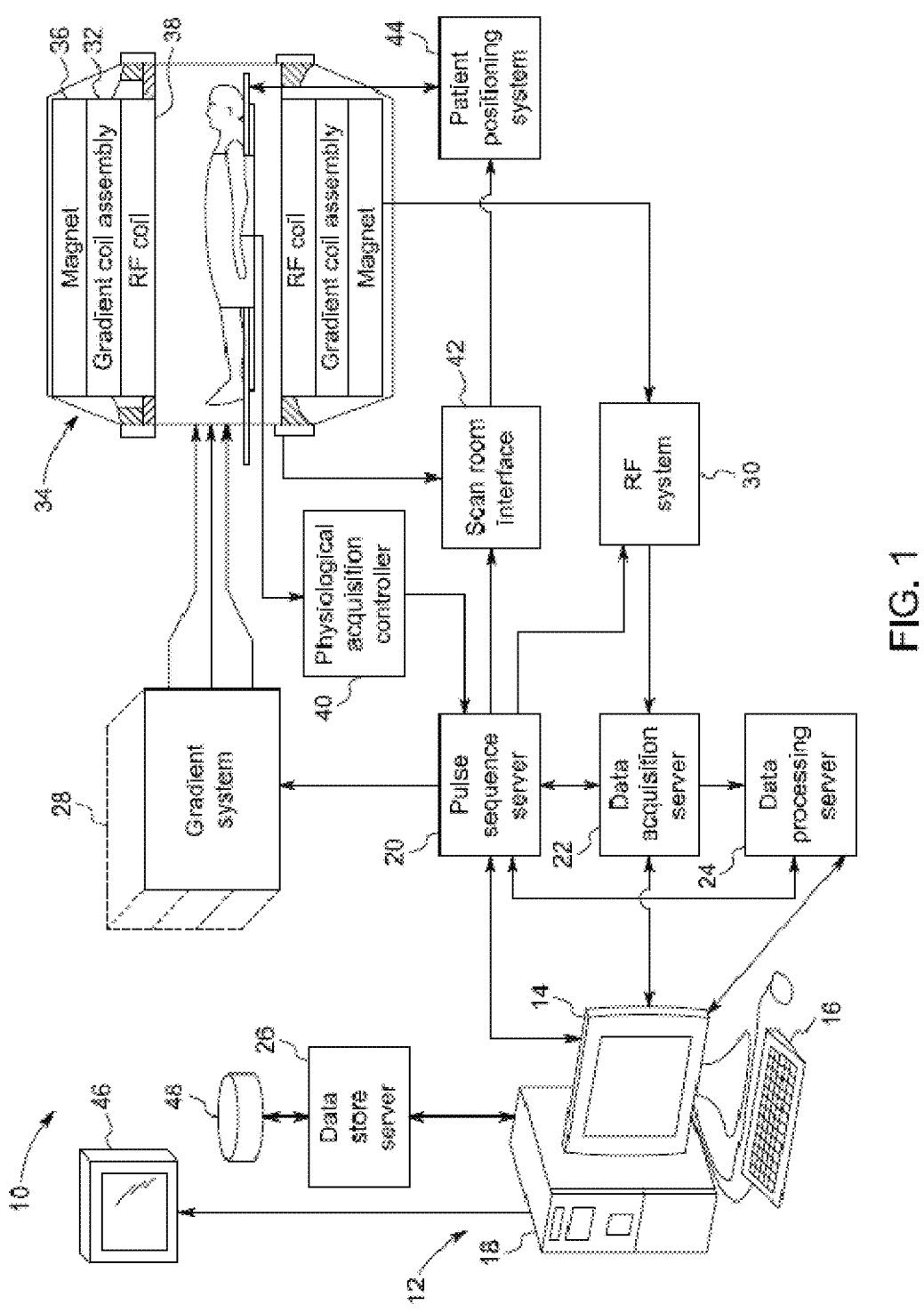
FIG. 1 is a schematic diagram of an example magnetic resonance imaging (MRI) system.

Unless otherwise indicated, the drawings provided herein are meant to illustrate features of embodiments of the disclosure. These features are believed to be applicable in a wide variety of systems including one or more embodiments of the disclosure. As such, the drawings are not meant to include all conventional features known by those of ordinary skill in the art to be required for the practice of the embodiments disclosed herein.

DETAILED DESCRIPTION

This disclosure includes systems and methods of mapping autoregulation of a subject. As used herein, a subject is a human, an animal, or a phantom, or part of a human, an animal, or a phantom, such as an organ or tissue. The kidney is used as an example for illustration purposes only. Systems and methods described herein may be applied to other organs outside the central nervous system of the subject. Method aspects will be in part apparent and in part explicitly discussed in the following description.

Autoregulation is an essential physiological process of the kidney, required to maintain renal blood flow and glomerular filtration rates. There are several critical mechanisms of local regulation of pressure and flow in healthy individuals, including the myogenic response and tubuloglomerular feedback (TGF). The myogenic mechanism arises from passive modulation of arterial diameter in response to fluctuations in blood pressure, protecting downstream glomerular capillaries from barotrauma and maintaining a relatively constant perfusion rate. The TGF mechanism may modulate glomerular arteriolar diameter to maintain local single-nephron glomerular filtration rates. The fluctuations in perfusion and arterial diameter associated with these mechanisms are known to normally occur at distinct bands of frequencies. However, these regulatory mechanisms become dysfunctional or are eradicated in hypertensive nephropathy and diabetes, and are strongly implicated in the progression of pathology and loss of kidney function associated with these diseases. There are several key gaps in the knowledge of intra-renal autoregulation over a human's life course. Autoregulation appears to be inefficient in the developing kidney and is impaired in the aging population. Current known methods to measure autoregulation of the kidney do not provide spatial information, and are invasive and not translatable to humans. For example, optical imaging may be used to map autoregulation by monitoring changes in vessel diameter, but the light does not penetrate through the skin and the abdominal tissue deep enough to image kidney.

Functional MRI (fMRI) has been used to study and diagnose brain cognitive functions and neural connectivity based on observations that when neural activities increase in a particular area of the brain, magnetic resonance (MR) signals increase by a small amount in that particular area because of an effect called the blood oxygenation level dependent (BOLD) effect, where increased neural activities reduce the oxygenation level in the blood and change the susceptibility of the tissue, causing changes in MR signals. During resting-state fMRI or resting state MRI, the subject is at rest. The subject lies in the MR scanner for a period of time with eyes closed or staring at a fixed point while BOLD data is acquired.

Since the development of resting state MRI decades ago, resting state MRI has been limited to the central nervous system such as the brain to study the neural function, and has never been applied to organs outside the central nervous system such as the kidney. The main reason is that known resting state MRI relies on the BOLD effect and is used to examine cognitive function and neural connectivity of the brain. The kidney does not have cognitive function or neural connectivity, and instead performs filtration of blood, rendering known resting state MRI insensible to be applied to the kidney. Similarly, the kidney's filtration functions and TGF mechanisms do not exist in the brain. Resting state MRI therefore does not appear to be a readily viable tool to map kidney function. Further, in the brain, perfusion and extraction of oxygen are tightly coupled to neural activity, providing the BOLD effect. In contrast, extraction of oxygen in the kidney is coupled to glomerular filtration. Accordingly, the major sources of the signal changes from the BOLD effects detected using known resting state MRI are different in the kidney than in the brain and analysis in the known resting state MRI for the brain is not readily applicable to the kidney. In addition, there is a long-felt need to monitor regulation of TGF in subjects, especially in response to drugs in subjects with diseases. The brain does not have TGF because brain does not have tubular structures or perform filtration. Accordingly, a person in the art would not have been motivated to translate resting state brain analysis to monitor TGF or autoregulatory functions of the kidney.

Systems and methods described herein address the above problems in known methods of mapping kidney functions and provide a noninvasive imaging tool to map autoregulation throughout the whole kidney, where autoregulation may be detected in the cortex of the kidney and in the medulla of the kidney. The systems and the methods described herein may be used to monitor regulation of autoregulation in subjects.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as $B_0$ and extends in the longitudinal or z direction. In acquiring an MRI image, a magnetic field (referred to as an excitation field $B_1$), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal $B_1$ is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

FIG. 1 illustrates a schematic diagram of an example MRI system 10. In the example embodiment, MRI system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MRI system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and a radiofrequency ("RF") system 30. The instructions are used to produce gradient and RF waveforms in MR pulse sequences. In MR, a pulse sequence is a sequence of RF pulses, gradient pulses, and data acquisition applied by MRI system 10 in acquiring MR signals. An RF coil 38 and a gradient coil assembly 32 are used to perform the prescribed MR pulse sequence. RF coil 38 is shown as a whole body RF coil. RF coil 38 may also be a local coil that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient coil assembly 32 to produce the magnetic field gradients $G_x$, $G_y$, and $G_z$ used for position-encoding MR signals. Gradient coil assembly 32 forms part of a magnet assembly 34 that also includes a polarizing magnet 36 and RF coil 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil 38 by RF system 30. Responsive MR signals detected by RF coil 38 are received by RF system 30, amplified, demodulated, filtered, and digitized under direction of commands produced by pulse sequence server 20. RF coil 38 is described as a transmit and receive coil such that RF coil 38 transmits RF pulses and detects MR signals. In one embodiment, MRI system 10 may include a transmit RF coil that transmits RF pulses and a separate receive coil that detects MR signals. A transmission channel of RF system 30 may be connected to a RF transmission coil and a receiver channel may be connected to a separate RF receive coil. Often, the transmission channel is connected to the whole body RF coil 38 and each receiver section is connected to a separate local RF coil.

In the example embodiment, RF system 30 also includes one or more RF receiver channels. Each RF receiver channel includes an RF amplifier that amplifies the MR signal received by RF coil 38 to which the channel is connected, and a detector that detects and digitizes the/and Q quadrature components of the received MR signal. The magnitude of the received MR signal may then be determined as the square root of the sum of the squares of the I and Q components as in Eq. (1) below:

$$M = \sqrt{I^2 + Q^2}; \qquad (1)$$

and the phase of the received MR signal may also be determined as in Eq. (2) below:

$$\varphi = \tan^{-1}\left(\frac{Q}{I}\right). \qquad (2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

Figure 2A:
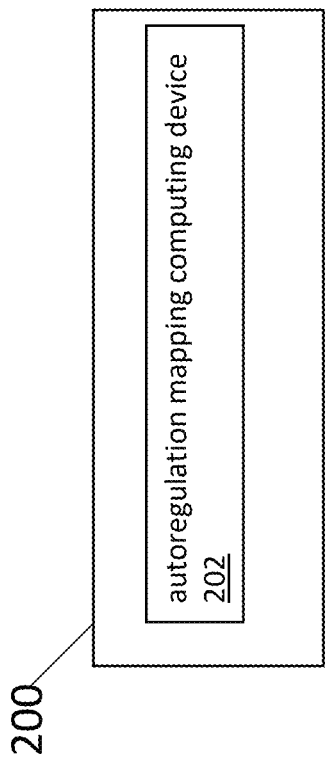
FIG. 2A is an example autoregulation mapping system.

FIG. 2A is a schematic diagram of an example autoregulation mapping system 200. In the example embodiment, system 200 includes an autoregulation mapping computing device 202 configured to map autoregulation of a kidney. The autoregulation mapping computing device 202 may be included in workstation 12 of MRI system 10, or may be included in a separate computing device that is in communication with workstation 12, through wired or wireless communication. In one example, autoregulation mapping computing device 202 is a server computing device, and may be cloud-based. In some embodiments, autoregulation mapping computing device 202 is a separate computing device from workstation 12 and receives MR images acquired by workstation 12 through a portable storage device, such as a flash drive or a thumb drive.

Figure 2B:
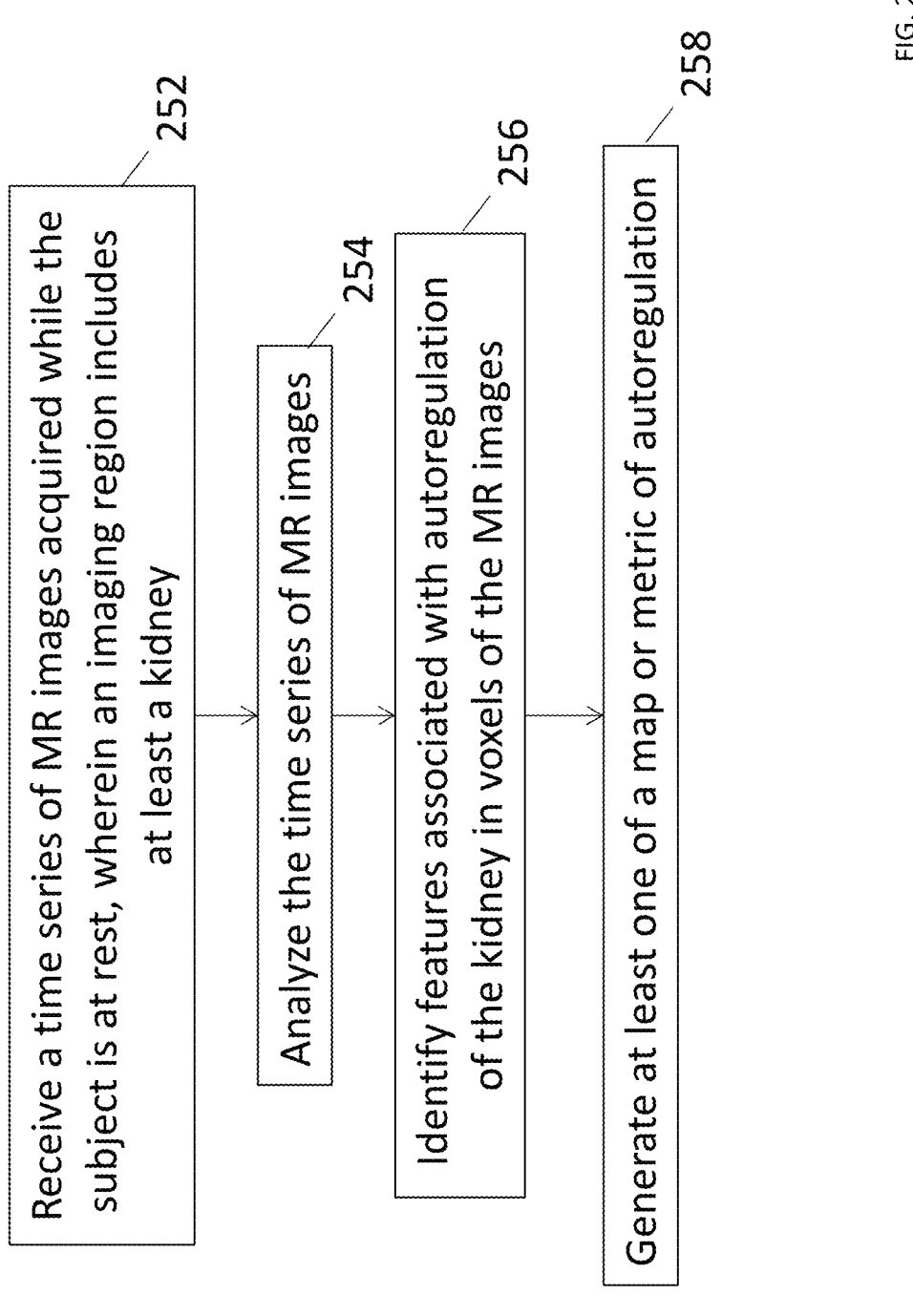
FIG. 2B is a flow chart of an example method of mapping autoregulation.
Figure 2C:
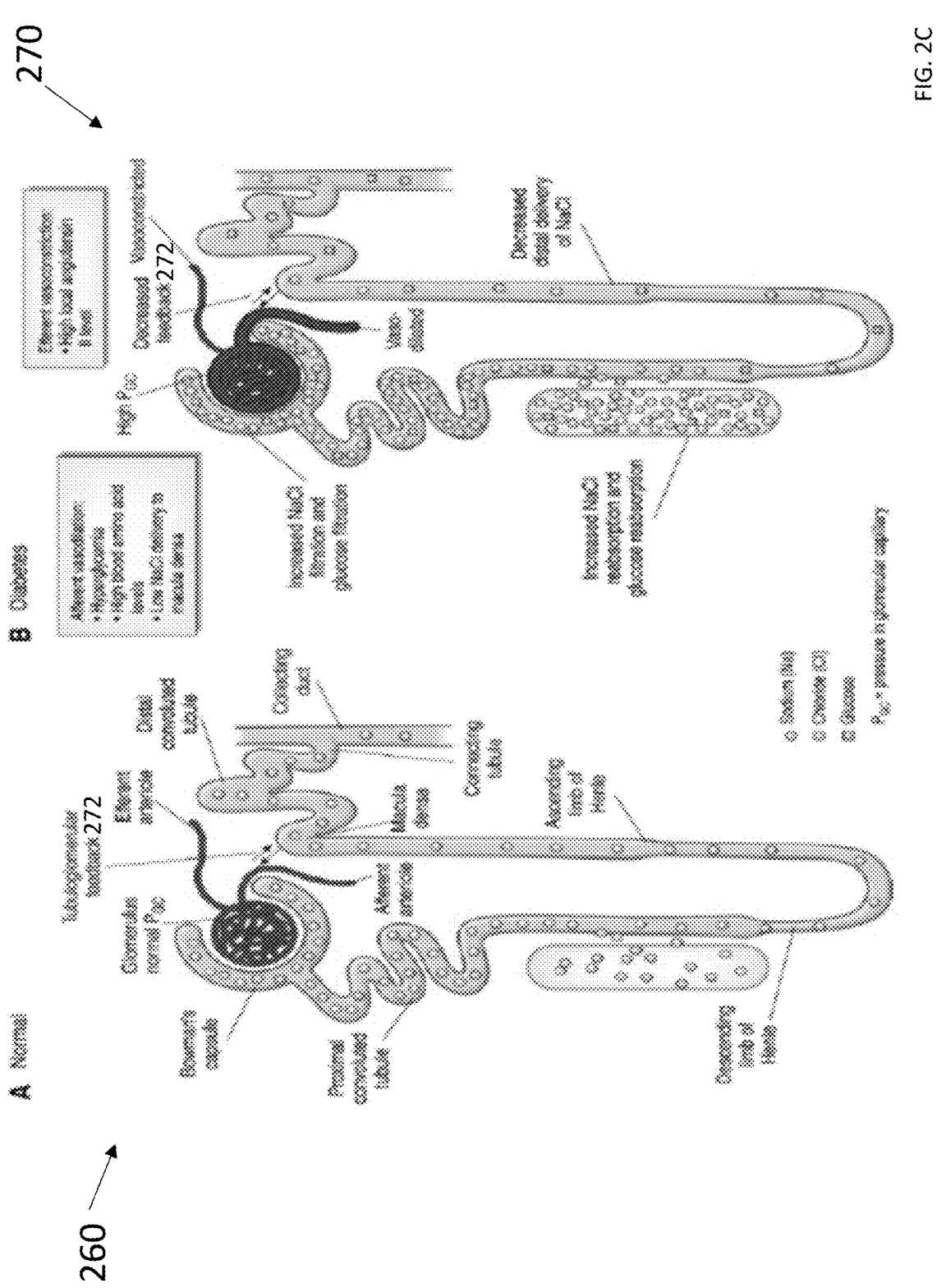
FIG. 2C are diagrams of the physiological function of the kidney.

FIG. 2B is a flow chart of an example method 250 of autoregulation mapping. The Method 250 may be implemented using autoregulation mapping computing device 202. FIG. 2C includes schematic diagrams of kidney autoregulation function. Diagram 260 shows the autoregulation of a normal subject. Diagram 270 shows the autoregulation of a subject with a disease such as diabetes. A disease affects the autoregulation of the subject. For example, as shown in diagram 270, in a subject with diabetes, the TGF 272 is decreased. Features associated with autoregulation and changes in autoregulation are not patently noticeable by merely visually examining anatomical MR images. The systems and methods described herein are advantageous in providing a map and/or metric of autoregulation based on a time series of noninvasively acquired MR images, unlike known methods such as optical imaging, which requires invasive probing to detect usable signals.

In the example embodiment, method 250 includes receiving 252 a time series of MR images acquired while the subject is at rest, where the subject is not performing a task or responding to stimuli such as viewing a picture or tapping fingers. The subject may passively receive a physiological challenge or exogenous manipulation to examine effects on autoregulation from the exogenous manipulation. Exogenous manipulation includes receiving a bolus of injection or delivery of drug or fluid such as sodium fluid, undergoing electrical stimulation, and/or maintaining a metabolic clamp such as a hyperglycemic or hypoglycemic clamp where the value of the metabolite is kept constant while checking responses to other variables. For example, the level of glucose in the body is kept constant and functional changes are observed by varying variables such as insulin or other variables such as pressure, flow, TGF, and myogenic responses. The imaging region of the MR images includes at least a kidney of the subject. Acquiring a time series of MR images while the subject is at rest may be referred to as resting state MRI. The images may be acquired as slices of 2D images or 3D images of a 3D volume. Images of the same imaging region are acquired repeatedly over a period of time. The time interval between the repetition may be referred to as time of repetition (TR).

In the example embodiment, method 250 further includes analyzing 254 the time series of MR images. The analysis is performed on time series of voxels by analyzing the time series of voxels and/or the relationship of the time series of one voxel with the time series of another voxel. For example, a time series of a voxel may be derived from the time series of MR images as a times series of signals at the voxel in the temporal dimension. Analysis is performed on time series of voxels, such as computing power spectra at the voxels based on the time series of corresponding voxels, or computing cross correlations between a time series of one voxel and a time series of another voxel/reference time series, power spectra of two voxels/one voxel with a reference power spectrum, or power spectra of a spectral band with a reference time series. The reference time series may be time series, power spectrum, or power spectrum of the spectral band corresponding to a reference voxel. A reference voxel may be a voxel in the MR images.

In the example embodiment, method 250 also includes identifying 256 features associated with autoregulation of the kidney in voxels of the MR images. The features may be spatial features such as voxels in the MR images. The features may be temporal features such as time series, power spectra, power spectra of spectral bands. Method 250 further includes generating 258 at least one of a map or metric of the autoregulation based on the identified features. A map of autoregulation may be generated based on the identified features by generating a map with identified spatial features highlighted on the MR images. Metrics of autoregulation may be measurements of the time series, power spectra, or power spectra of spectral bands, such as phases, magnitudes, or areas under the curves or parts of the curves. The measurements may be based on individual voxels or a plurality of voxels. Method 250 also include outputting at least one of the map or the metric. The map and/or metric may be displayed on a user interface of autoregulation mapping computing device 202.

For example, features corresponding to myogenic responses may be identified as voxels having peaks in or areas under the frequency range corresponding to myogenic responses above a threshold level. Features corresponding to TGF may be identified as voxels having peaks in or areas under the frequency range corresponding to TGF above a threshold level. Myogenic responses may have a frequency in a first frequency range, which is referred to as a myogenic band herein. TGF may have a frequency in a second frequency range, which is referred to as a TGF band herein. The myogenic band does not usually overlap with the TGF band, and has a higher frequency over the TGF band. For example, the myogenic band may be in the range from 100 mHz to 300 mHz, and the TGF band may be in the range from 0 to 100 mHz. Besides myogenic responses and TGF mechanisms, other autoregulatory mechanisms may be detected using the systems and methods described herein. Other autoregulatory mechanisms may be at different frequencies. For example, there may be a BOLD effect, which is at a frequency lower than the frequencies corresponding to myogenic responses and TGF mechanisms. Other examples of features include autoregulatory responses to autonomic nervous system stimulation or hormonally driven changes in blood flow or pressure.

Maps of individual mechanisms of autoregulation may be generated using features corresponding to the individual mechanisms. Maps for mechanisms may be combined in any manner by combining features of individual mechanisms in that manner. Metrics of autoregulation may be generated based on the temporal features where the metrics are measurements of the temporal features.

Maps of autoregulation may be generated using features determined based on cross correlations.

Local correlations between magnitude spectra or spectral bands, where a cluster of voxels have relatively high cross correlations such as being above a threshold level with a reference voxel in the cluster, indicate features corresponding to regions of nephrovascular units. Long-range correlations between magnitude spectra or spectral bands, where voxels have relatively high cross correlations such as being above a threshold level with the magnitude spectrum or spectral band of a reference voxel, indicate features corresponding to coordination between different regions of the kidney to maintain glomerular filtration.

Loss of correlation between regions, reduced correlation, or reduced range of spatial correlation, where voxels have reduced cross correlations with a reference time series, may indicate features corresponding to disruption in autoregulation associated with disease. Diseases that affect autoregulation are numerous, but examples include hypertensive nephropathy, diabetic nephropathy, or lupus nephritis that change arterial vascular resistance or alter the timing of response of the vasculature to changes in sodium excretion or blood pressure. Specific pathologies that affect autoregulation include fibrosis and sclerosis, which are observed in many diseases. Other conditions in other organs that affect autoregulation include cirrhosis and congestive heart failure. Identifying changes in cross correlations may be useful to assess extent of kidney damage. Identifying changes in correlations between regions or within regions provide tools to detect early disease progression, which is advantageous because there are no clinical or noninvasive tools to detect kidney disease at an early enough stage to prevent progression to end stage kidney disease.

Vasoaltering agents/molecules such as Angiotensin II, or drugs, affect autoregulation. Thus, monitoring autoregulation correlation may be useful to assess response to therapies. Systems and methods described herein therefore provide tools to potentially identify the correct timing and measure the efficacy of therapies to mitigate hypertension and nephropathy. In addition, systems and methods described herein provide tools to sensitively and noninvasively assess the health or functional capacity of living or deceased donor kidneys as candidates for transplantation. These tools also allow assessment of function or loss of function in regions of the kidney that will be or have been removed or affected by surgical procedures, such as in removal of a tumor.

Small animals such as rats are described as examples only. The systems and methods may be used to map autoregulation of human kidney. In acquiring MR images of a human kidney, different coils are used to accommodate different sizes of the subject. Pulse sequences and protocols may be adjusted for human subjects. For example, the heart rates and respiration rates are different in humans than in rats. TR is accordingly adjusted to reduce aliasing errors from cardiac and respiratory signals.

The Kidney is used as an example for illustrative purposes only. Systems and methods described herein may be applied to other organs outside the central nervous system, such as the musculoskeletal system, skin, eyes, liver, spleen, heart, and lungs. Organs outside the central nervous system do not have brain activities. The systems and methods described herein are advantageous in generating maps/metrics of the autoregulation functions in the organs, unlike known methods of resting state brain imaging. Maps and/or metrics of autoregulation in other organs are generated based on series of MR images of the organs, by applying the analysis described here. Systems and methods described herein may be applied to generate maps and/or metrics of interorgan correlation. For example, a time series of MR images of organs of interest such as the liver and the kidney are acquired. Interorgan correlations between the MR detected oscillations or fluctuation across the organs are determined by determining the cross-correlations of the time series, relative phase differences, power spectra of time series, and/or cross-correlations of power spectra of voxels in a first organ, such as the kidney, with those of voxels in a second organ, such as the liver.

Figure 3:
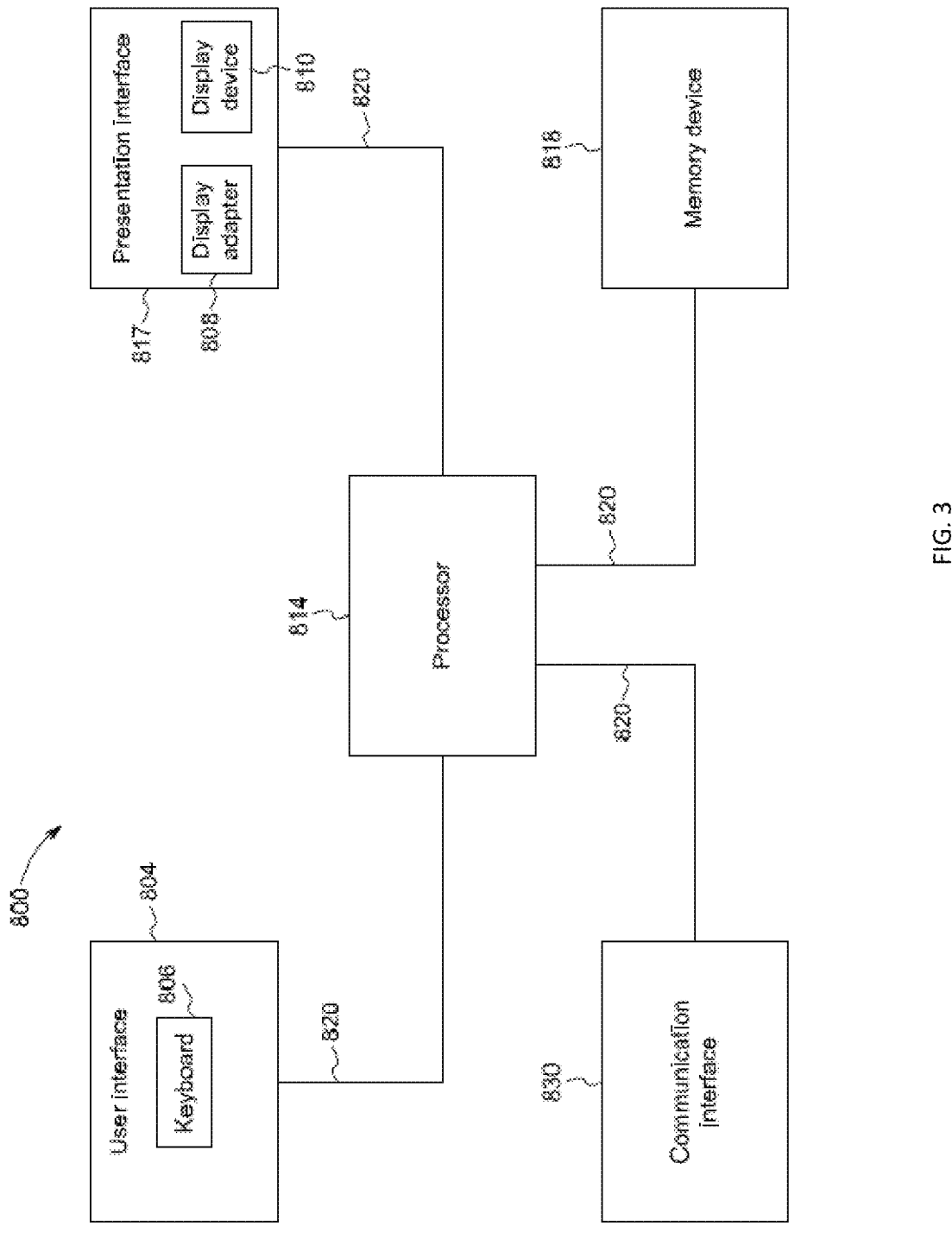
FIG. 3 is a block diagram of an example computing device.

Workstation 12 and autoregulation mapping computing device 202 described herein may be any suitable computing device 800 and software implemented therein. FIG. 3 is a block diagram of an example computing device 800. In the example embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the example embodiment, computing device 800 includes a presentation interface 817 that presents information, such as input events and/or validation results, to the user. Presentation interface 817 may also include a display adapter 808 that is coupled to at least one display device 810. More specifically, in the example embodiment, display device 810 may be a visual display device, such as a cathode ray tube (CRT), a liquid crystal display (LCD), a light-emitting diode (LED) display, and/or an "electronic ink" display. Alternatively, presentation interface 817 may include an audio output device (e.g., an audio adapter and/or a speaker) and/or a printer.

Computing device 800 also includes a processor 814 and a memory device 818. Processor 814 is coupled to user interface 804, presentation interface 817, and memory device 818 via a system bus 820. In the example embodiment, processor 814 communicates with the user, such as by prompting the user via presentation interface 817 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the example embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the example embodiment, memory device 818 stores, without limitation, application source code, application object code, configuration data, additional input events, application states, assertion statements, validation results, and/or any other type of data. Computing device 800, in the example embodiment, may also include a communication interface 830 that is coupled to processor 814 via system bus 820. Moreover, communication interface 830 is communicatively coupled to data acquisition devices.

In the example embodiment, processor 814 may be programmed by encoding an operation using one or more executable instructions and providing the executable instructions in memory device 818. In the example embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Figure 4:
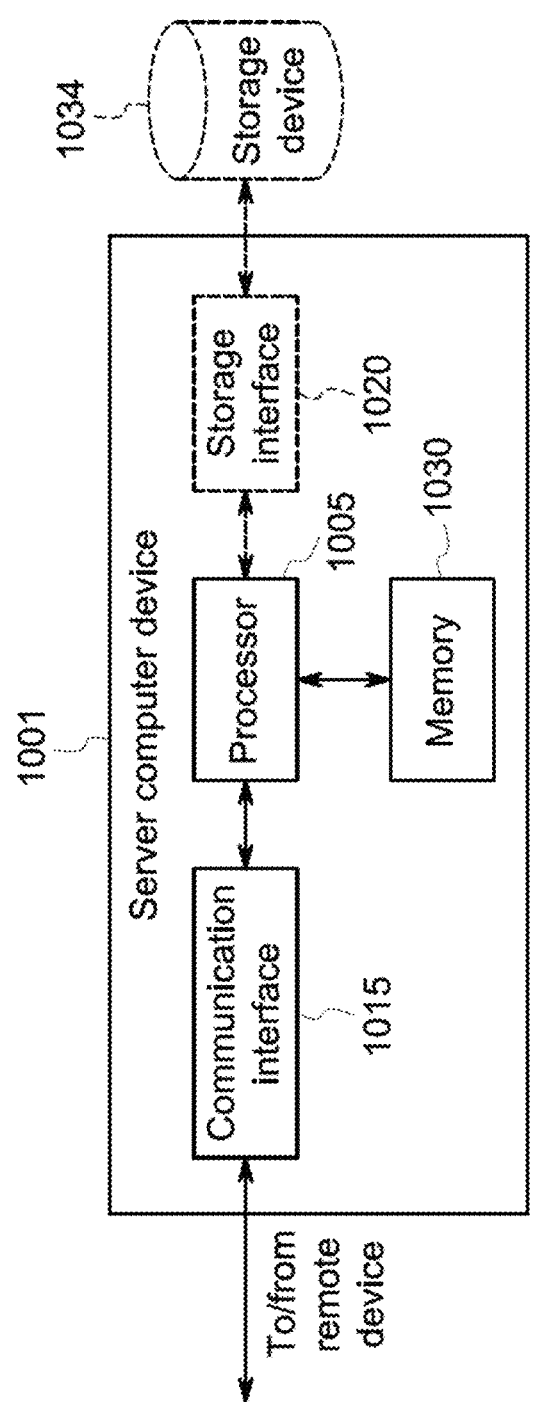
FIG. 4 is a block diagram of an example server computing device.

FIG. 4 illustrates an example configuration of a server computer device 1001 such as computing device 202. Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device or another server computer device 1001. For example, communication interface 1015 may receive data from workstation 12, via the Internet.

Processor 1005 may also be operatively coupled to a storage device 1034. Storage device 1034 is any computer-operated hardware suitable for storing and/or retrieving data. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of independent disks (RAID) configuration. storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

EXAMPLES

Example 1

A. Summary

We propose to develop resting-state magnetic resonance imaging (MRI) as a tool to measure autoregulation of the kidney. In one example, we observed spatially variable, low-frequency (0.01-0.2 Hz) fluctuations in the MRI signal in the rat kidney, using a simple 10-15 minute non-contrasted scan. The fluctuations are 1-2 orders of magnitude slower than the respiratory rate, and are consistent with known frequencies of both the myogenic response (~0.2 Hz) and tubuloglomerular feedback (TGF, ~0.01 Hz). Resting-state MRI has never been applied to the kidney before, since the use of resting-state MRI to map low-frequency oscillations that reflect functional connectivity and autoregulation in the brain decades ago. Here, we will evaluate the resting state signal at the scale of individual nephrons, in vivo, examining the rat kidney across the lifespan. Next, we will map the frequency spectrum of autoregulation in a rat model of hypertension to understand how these mechanisms are correlated between regions of the kidney and in disease progression. The method will provide a new, noninvasive tool to measure the autoregulatory mechanisms of the kidney.

Mapping myogenic and TGF mechanisms of autoregulation in the kidney using resting-state MRI is provided. We will develop the tool of resting-state MRI to measure changes and spatial correlations of the observed fluctuations, mapping them in 3D to individual glomeruli and associated vasculature. Resting state MRI may sensitively detect and distinguish myogenic and TGF responses of autoregulation in the rat kidney.

Firstly, resting-state MRI may be used to map spontaneous fluctuations associated with auto-regulation of the healthy rat kidney throughout life. We will image the rat kidney across the life course and optimize the MR imaging to rapidly map the resting-state spectrum in each voxel. We will modulate the myogenic and the TGF responses pharmacologically to confirm the source of the fluctuations. We will validate the MRI spectrum by measuring changes in vascular diameters optically in specific locations in animals from each cohort, directly co-registered with the MR images. Finally, we will examine spatial correlations in the mapped time-courses to identify patterns of function consistent with coupling between nephrons and the vasculature.

Secondly, resting state MRI may be used to detect decreased myogenic and TGF responses during development of nephropathy in the spontaneously hypertensive rat (SHR). We will perform the same resting-state MRI experiments in the SHR at time points spanning development of hypertensive nephropathy, mapping the power spectra of the time courses and their spatial patterns in the myogenic and TGF frequency bands relative to anatomical structures.

The outcome of this work will be a new "lens" through which to evaluate autoregulation in the kidney, and a better understanding of the impact of autoregulation on short- and long-term outcomes in disease and therapies. These noninvasive, noncontrasted metrics may be used in genetically engineered animal models to view kidney pathophysiology, or applied in patients to assess the quality of kidney allografts. Mapping autoregulation throughout the kidney provides a new spatially-informed perspective to investigate biomarkers of kidney health or response to therapies.

B. Strategy

The kidney maintains glomerular filtration and osmotic regulation of the blood, despite constant and potentially damaging natural fluctuations in systemic blood pressure. There are several identified mechanisms of autoregulation of local blood pressure and flow, including a myogenic response and TGF. The myogenic response arises from passive modulation of arterial diameter in response to systemic blood pressure fluctuations, protecting the downstream glomerular capillaries from barotrauma. The TGF mechanism arises from signaling by the macula densa to modulate glomerular arteriolar diameter in response to changes in NaCl concentration in the distal convoluted tubule. These two mechanisms become dysfunctional in pathologies associated with diabetic and hypertensive nephropathy, due in part to glomerular and tubular injury from uncontrolled fluctuations in pressure. Each mechanism is associated with distinct, but spatially variable bands of low-frequency fluctuations in perfusion rates and arterial diameters. The myogenic response causes fluctuations in the myogenic band, and the TGF in the TGF band. Some diseases may affect the autoregulation function such that fluctuations in the myogenic response and/or TGF fall outside the corresponding typical bands of the myogenic band and/or the TGF band of a normal subject. Optical imaging may be used to validate that the outside bands correspond to the myogenic response and/or the TGF, using models, such as small animal models. Currently, there are no clinically translatable tools to measure and map autoregulation in the kidney. We propose to measure these fluctuations using MRI. There are three likely ways that autoregulatory functions change the MRI signal: 1) Tissue motion due to changes in arterial diameter, 2) Changes in local flow due to changes in arterial diameters, and 3) Changes in blood oxygenation (primarily in the medulla) due to oxygen uptake or hypoxia, causing a change in red blood cell paramagnetism.

B.1. Significance

Previous studies of autoregulation in the kidney have been limited to micropuncture of single nephrons or measurements of mean arterial pressure. However, nephrons and vasculature are coupled in "nephrovascular units" (NVUs) that reflect the geometry and oxygen demands of the individual kidney. Kidney anatomy and function is highly heterogeneous, and autoregulation likely varies with location and between individuals. This complex system driving local and organ-level myogenic and tubuloglomerular feedback is less efficient in the young, is impaired with aging, and is diminished in kidney diseases associated with hypertension and diabetes. These regulatory systems are not fully developed in the preterm or young neonate, and may contribute to the development of acute kidney injury (AKI). Understanding autoregulation is therefore needed to guiding therapies, not only to prevent AKI but also to treat disease progression in patients with hypertensive nephropathy. Mapping autoregulation throughout the kidney by MRI provides a spatially-informed perspective through which to view kidney pathophysiology, and may provide new, noninvasive biomarkers of kidney health and response to therapies. Resting-state MRI may also be used in combination with optical and genetic techniques in preclinical studies to investigate how specific genes or cells contribute to kidney physiology. This work will provide a noninvasive tool to more completely understand mechanisms and develop predictive markers to investigate genetic models, guide new therapies, inform allograft transplantation, and monitor kidney health.

B.2. Systems and Methods

The systems and methods described here provide: 1) First investigation of resting state physiological fluctuations and spatial correlations in the whole kidney, in vivo. 2) Direct localization of physiological fluctuations to individual nephrons. 3) New, noninvasive imaging biomarkers that may be directly translated to human studies. 4) Novel investigation of the physiological mechanisms and time course of autoregulatory failure during development of spontaneous hypertension in the rat.

C. Approach

Our investigations are aimed at mapping and validating the resting state MRI signal in the kidney, in vivo. We have established the feasibility of all of the proposed experiments, based on our established technologies and preliminary studies.

Figure 5:
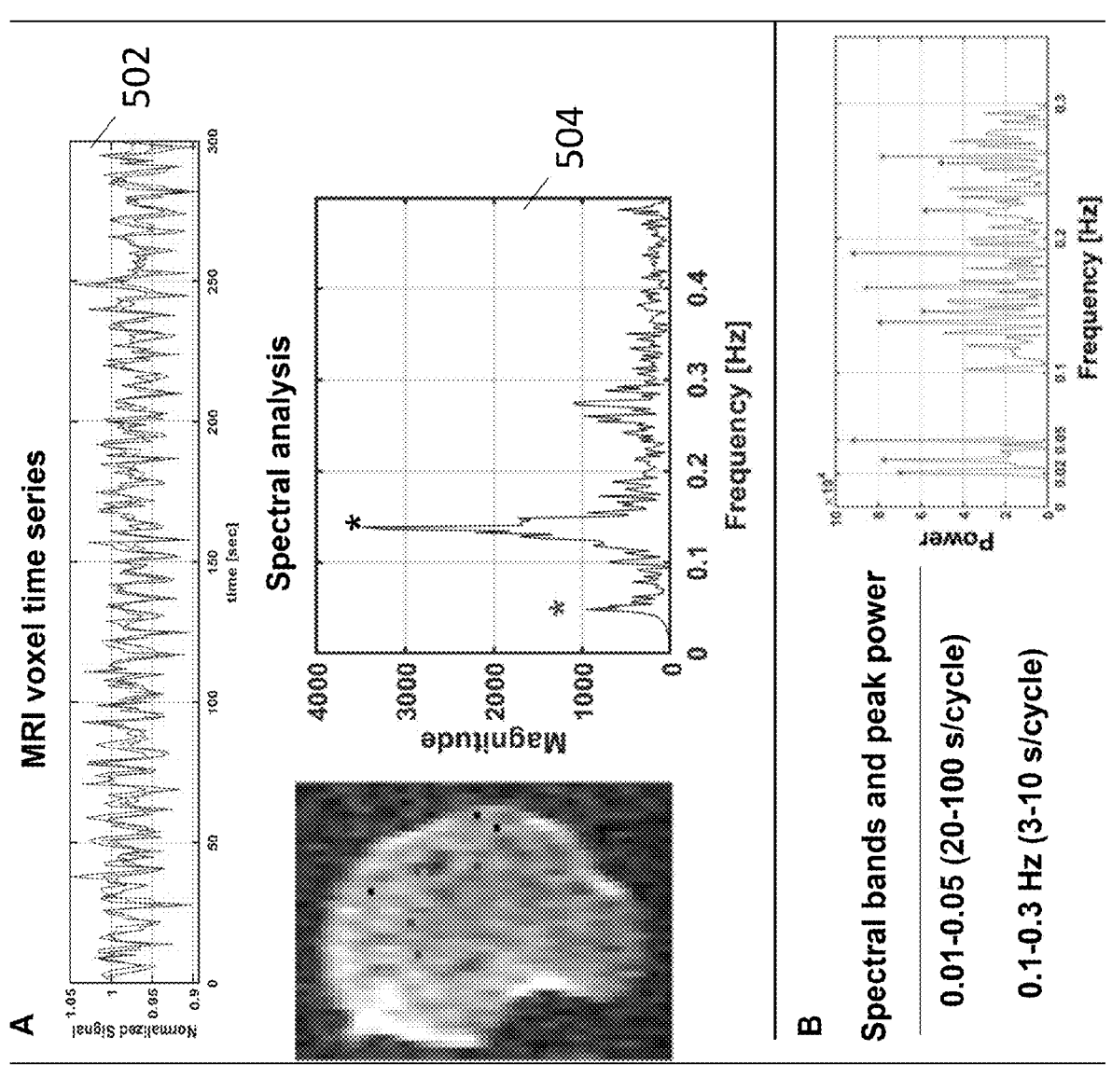
FIG. 5 shows results of resting state MRI of a kidney.

C.1. Preliminary study 1: Detection of spatially variable, low-frequency fluctuations in the rat kidney, in vivo, at rest. We first established the feasibility of MRI to detect low-frequency fluctuations in vivo. We performed resting-state MRI (Spin-echo EPI 9.4T) over 10 minutes in anesthetized rats (n=3), gating acquisition, controlling respiration and temperature, and monitoring pulse. Signals from respiration (~1.5 Hz) and the heartbeat (~5 Hz) aliased into the low frequency spectrum (0.01-0.3 Hz) using repetition time (TR)=500 ms or 1 s, but not at TR=250 ms, so we used TR=250 ms. We acquired time series from all voxels in cortex, medulla, and vasculature, and performed power spectral analysis. Image resolution was 300 μm in each dimension, and images were acquired every 250 ms, with multi-slice acquisition. FIG. 5 shows results of in vivo resting state spin-echo EPI MRI of the rat kidney. FIG. 5 are time series and power spectra from cortex. A) includes a 2D image slice of kidney with noted voxels (colored dots) in medulla (red) and cortex (black). An example of three time-series of neighboring cortical voxels is shown in plot 502, with clear low frequency oscillations. Plot 504 is spectral analysis or a power spectrum of a voxel time-series reveals spatially variable fluctuations in cortex and medulla in frequencies (red and black stars) and averaged across voxels in B) bands consistent with frequencies of tubulo-glomerular feedback and myogenic auto-regulatory mechanisms. A power spectrum at each voxel may be computed by Fourier transforming the time series corresponding to the voxel based on the time series of MRI images acquired in resting state MRI and taking the squared magnitude of the Fourier transformed time series. We observed significant spectral peaks ~10,000× above noise power in the two bands of interest: a myogenic band of 0.1-0.3 Hz and a TGF band of 0.02-0.05 Hz. The number and peak frequencies within these bands were spatially variable, with significantly (p<0.05) more total power and variability in the myogenic band. Peaks in the TGF band were heterogeneously distributed in cortex and varied in power, consistent with localization to the glomeruli. All rats exhibited spectra of spectral peaks ~10,000× above noise power in the TGF band and the myogenic band.

C.2. Preliminary study 2: Establishing the SHR model in our laboratory and confirming vascular pathology. We proposed to examine resting state fluctuations in the spontaneously hypertensive rat (SHR). To confirm the vascular pathology, we examined 12 SHR compared to age matched Wistar-Kyoto controls (WKY) from age 16 weeks through development of hypertension and nephropathy at 34 weeks. We tracked blood pressure using a tail cuff. We performed histopathology with sections stained with Masson's trichrome at 34 weeks. A renal pathologist examined the slides. Blood pressures were SHR: 157/117 at 34 weeks vs WKY controls: 113/95. Pathology revealed intermittent fibrosis in SHR in interstitium and fibrosis around arterioles but not in WKY. These preliminary data support our expectation to track development of altered, spatially variable autoregulation during the proposed experiments.

Figure 6:
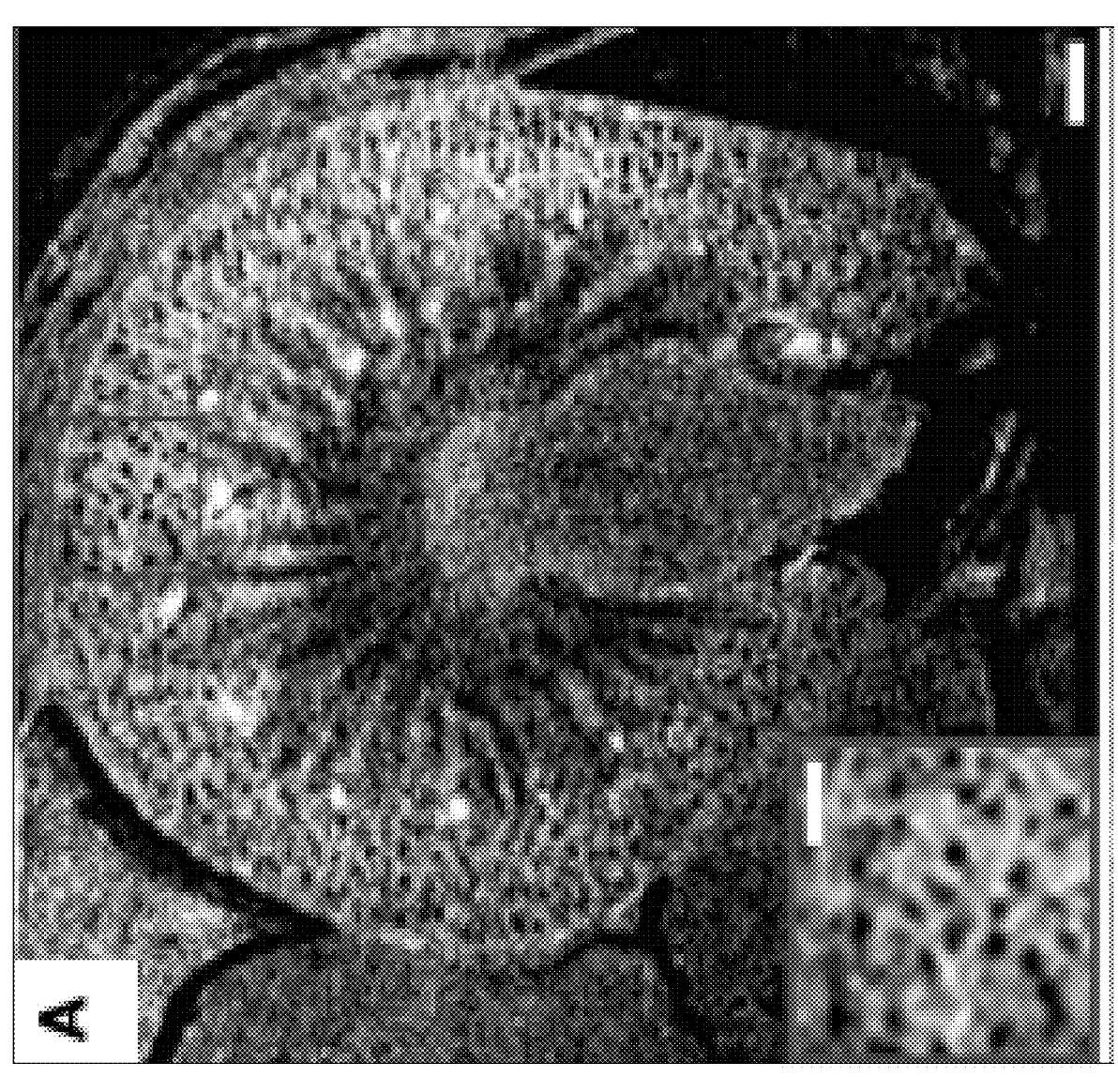
FIG. 6 is a cationic ferritin enhanced MR image of a kidney.

C.3. Preliminary study 3: co-localization of function and individual nephrons in 3D in MRI. Our team has developed imaging tools to noninvasively evaluate kidney structure and function. We have developed several technologies, including cationic ferritin enhanced MRI (CFE-MRI) to identify each functioning nephron from 3D MR images. We have used CFE-MRI to anatomically localize other imaging biomarkers. Our software produces three-dimensional maps across contrast techniques and modalities. An example of in vivo CFE-MRI of the rat kidney is shown in FIG. 6. FIG. 6 shows in vivo CFE-MRI may be used to measure nephron mass in a rat. Axial 2D slice of a 3D CFE-MRI dataset of a rat kidney in vivo showing glomeruli detected as punctate dark spots in cortex (inset). Here, we will perform CFE-MRI after our dynamic resting-state MRI, allowing us to associate acquired voxel time series and spectra with individual glomeruli.

Figure 7:
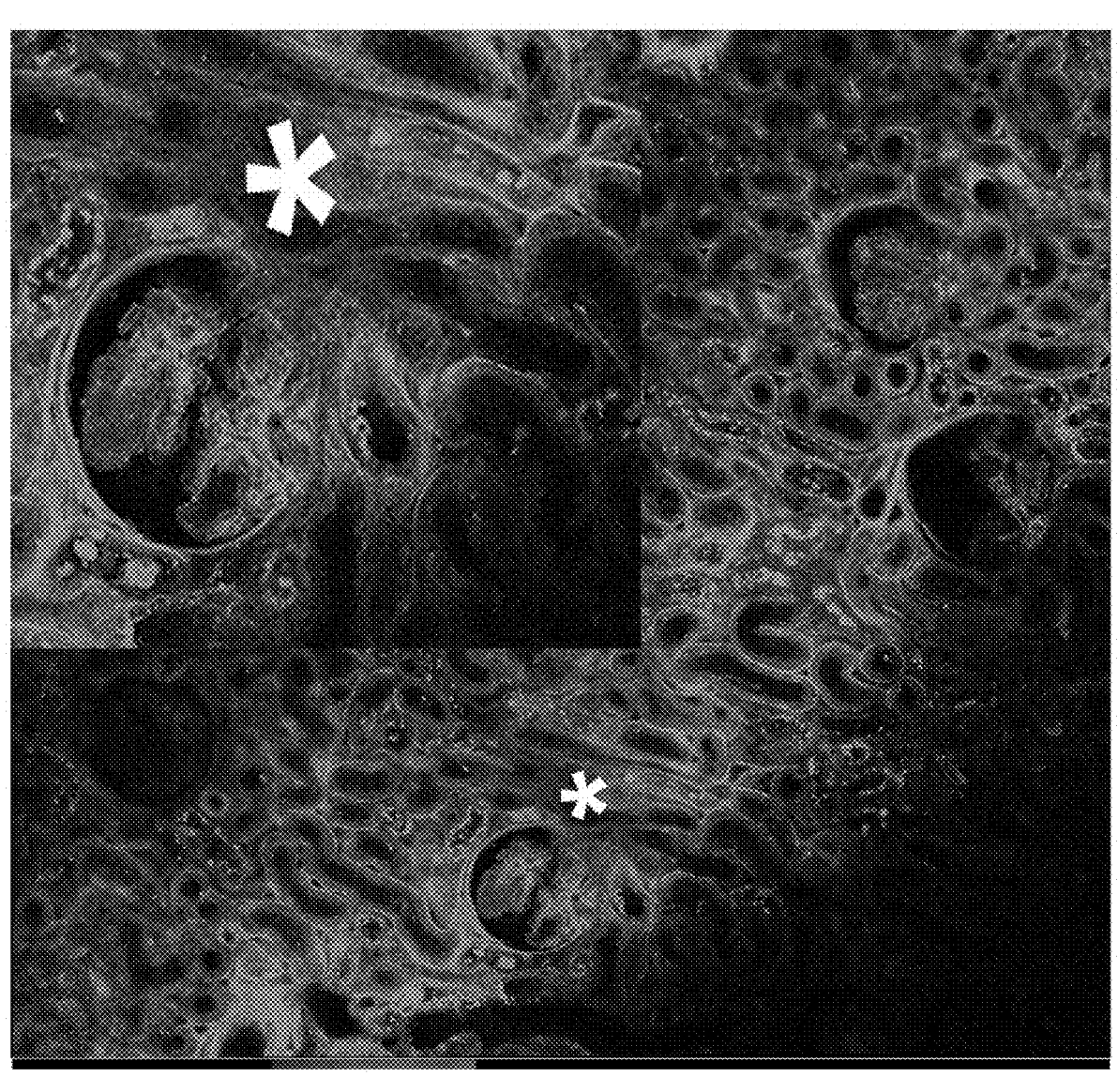
FIG. 7 is an optical image of a kidney.

C.4. Preliminary study 4: Validation using intravital optical microscopy. We will perform intravital optical imaging using a slide frame affixed to the externalized kidney. We have performed preliminary studies to establish this technique in our laboratory. We may select frames with vasculature and render them in 3D in Amira for analysis. FIG. 7 is an image of intravital optical microscopy of a Sprague-Dawley rat kidney, in vivo. Arterioles (star) and tubules are visible and may be reconstructed in 3D from z-stack. As shown in FIG. 7, glomeruli are easily identified. We have visualized an average of 50 glomeruli at a depth of 100 um (up to 1 mm). The Teflon frame (MRI-compatible) may be used to image the externalized kidney. The edge of the frame is visible in CFE-MRI, allowing us to co-register the same glomeruli in 3D between the optical images and the MR images. We have performed co-registration between optical imaging with MRI in rats, mice, and human kidneys with similar results.

C.5. Mapping myogenic and TGF mechanisms of autoregulation in the kidney using resting-state MRI. Resting-state MRI has been applied over the past two decades to detect spontaneous fluctuations associated with vascular autoregulation and to detect spatial correlations in blood oxygenation in the brain. Our preliminary studies using a modified acquisition techniques indicate the presence of spatially variable, spontaneous low-frequency fluctuations in the resting-state MRI signal in the rat kidney. The frequency bands of these fluctuations correspond to known frequencies associated with the myogenic and TGF mechanisms. We will establish the range and reproducibility of spectral bands and phase correlations of these fluctuations within and between healthy kidneys over the life course, and examine how they change with pharmacologic manipulation and with development of hypertension in the rat kidney, in vivo. We will validate our measurements using optical microscopy, and characterize the range of spectral power and timing between different glomeruli. Our experiments are designed to test the that resting state MRI may sensitively detect and distinguish myogenic and TGF responses of autoregulation in the rat kidney.

Design:

Cohort #1: Healthy Sprague Dawley rats.

Experiment A. Resting state MRI: We will perform resting-state MRI of the kidney of neonatal (1-2 weeks), young adult (10-12 weeks) and aged rats (18 months) using the MR imaging tools from our preliminary studies. MRI experiments are detailed in General Protocols. We will apply two MRI protocols in twelve Sprague Dawley rats (n=6/sex/age group) using our Bruker 9.4T scanner: 1) Spin-echo EPI (SE-EPI), as in our preliminary studies, and 2) Gradient-echo EPI (GRE-EPI). Advantages of SE-EPI are higher signal-to-noise ratio and our previous observation of spectral peaks using this sequence. The advantage of GRE-EPI is speed of acquisition, allowing us to achieve full 3D coverage within the same or shorter TR (~250 ms). Shorter TR may be beneficial for examining spatially heterogeneous changes in function due to pathology. The experiments will first be performed in vivo, then with externalization of the kidney in the live animal at each age, for assessing and minimizing the impact of abdominal motion. In a pilot experiment in each cohort (n=3 rats), we will vary the repetition time (TR) at low resolution (~3 mm³, beginning with TR=250 ms) and observe the spectra of a time course in regions of interest (ROIs) in cortex and medulla. In all animals, we will then perform 15 minutes of both SE-MRI and GRE-MRI random order (General Protocols). We will perform test-retest in three repetitions of each scan in three animals from each cohort to establish intra-subject reproducibility of the spectra in voxels and in tissue compartments (cortex, medulla, vasculature). We will then externalize the kidney, surgically exposing it and isolating it from the abdomen, and perform the same experiments including test-retest, eliminating aliasing by computing the aliased frequencies associated with the measured cardiac and respiratory frequencies. We will perform optical imaging in the six exposed kidneys (3 per sex from the 10-12 week cohort) to validate MRI measurements by comparing spectra of changes in arterial and arteriolar diameter with the observed spectral frequencies at the same locations. Vasculature may be detected using with autofluorescence. Alternatively, the rat may be injected with fluorescent dyes to identify and measure vasculature (fluorescent-conjugated albumin: Alexa-680 at 1300 nm or fluorescent-conjugated dextrans: Texas red at 860 nm). All kidneys will be imaged using a Nikon AIRMP two-photon microscope in the WashU Center for Cellular Imaging (WUCCI). Images in planes will be acquired at depths up to 500 um from the surface at 25 um increments.

Experiment B. Vascular and glomerular co-registration in MRI: After the resting-state scans of the externalized kidneys, we will inject CF and perform both T1-weighted 3D gradient echo and CFE-MRI (See General protocols) to map the vasculature and glomeruli for co-registration with the resting state MRI. This allows us to compute distance of the spectral features to major vasculature and relationship between both TGF and myogenic spectral components to individual glomeruli.

Experiment C. Inhibition of autoregulation: In another set of animals, we will inhibit the TGF response and diminish the myogenic response using furosemide. We will administer furosemide to healthy age-matched Sprague-Dawley rats intravenously at 10-12 weeks (n=6/sex) (bolus of (5 mg/kg) followed by furosemide drip of 5 mg/kg/h in saline to run throughout the imaging session). We will perform experiments A&B in triplication over 1.5 hours, both before and after furosemide administration.

Cohort #2 Spontaneously hypertensive rat (SHR): The SHR is a well-established model of hypertension and progression to nephropathy. The SHR will be divided into three age groups, each containing 12 animals (n=6/sex/group at 10-12, 24, and 34 weeks). Each cohort will also have age-matched Wistar-Kyoto (WKY) controls. We will measure blood pressure weekly using a tail vein cuff, as in our preliminary studies. We will measure glomerular filtration rate (GFR) every month and the day before MRI in each animal using the MediBeacon system (See Equipment). We will perform the MRI experiments from A&B as in Cohort 1 at each time point in the WKY rats (n=6/sex/time point). Our number of animals is based on power calculation using the expected inter-rat differences in spectral power in our preliminary studies. At the end of each experiment, we will euthanize and perfuse the animals and perform tissue histopathology of the imaged kidney. At euthanasia, a portion of the kidney will be immersion fixed in 4% formalin for histologic assessment. We will section and stain with hematoxylin and eosin and Siruis red as in our preliminary studies and quantify percent vessels and percent of interstitium with fibrosis.

Analysis and Expected Outcomes:

Frequency analysis: Spectral and phase and spatial correlation analysis will be performed. We will segment the 2D (spin echo) and 3D (gradient-echo) images, and co-register all images in Amira. We will use both AFNI and Matlab software to examine the time courses associated with each voxel. We will first perform linear de-trending and normalization to remove high-power low-frequency contamination of the spectra. We will compute the fast Fourier transform (FFT) and the power spectrum, comparing intra- and inter-cohort power from 0-0.5 Hz. Because frequencies associated with autoregulation may vary by ~25%, our comparisons will be performed in smaller sub-bands of 0.02 Hz in the TGF band and 0.1 Hz in the myogenic band, or ~10% the order of magnitude of the band of interest. We will perform ANOVA in each sub-band and peak with p<0.05 for significance. We will compare the spectra within and between cohorts, and within and across specific tissue compartments of cortex, medulla, and major vasculature. We will quantify the inter-voxel variation in the power spectra. We will reconstruct the vasculature from the T1-weighted images and the glomeruli from CFE-MRI. We will co-register the 3D T1-weighted MRI and glomerular maps to the resting state data in Amira. We will quantify differences in spectra in each voxel by distance from the vasculature and by whether or not the voxel contains a glomerulus. We will compare spectra from both SE-EPI and GRE-EPI in each tissue compartment to determine whether there is likely additional information from the GRE-EPI that reflects low-frequency fluctuations in blood oxygenation, particularly in medulla. We expect that SE-EPI is relatively insensitive to this blood oxygen effect, particularly in the cortex, allowing us to isolate the blood oxygen effect or BOLD effect from the effects of kidney autoregulation via myogenic responses and/or TGF.

Phase analysis: To examine spatially synchronous fluctuations possibly associated with nephrovascular units in each animal, we will analyze the phase-corrected cross-correlation of the time-series, creating maps of Pearson's correlation coefficient of each voxel with every other voxel. This type of analysis may be implemented in AFNI software. We will examine regions of statistically significant correlation (absolute correlation coefficient >0.75), rendering highly correlated regions in 3D relative to the vasculature. We will also identify regions that are anti-correlated (out of phase). We expect to find local clusters of voxels in cortex are coherent in phase in the TGF band, consistent with local coupling between clusters of nephrons and vascular supply. More voxels should have phase coherence in the myogenic band because this mechanism arises from larger vessels throughout the kidney.

Validation using optical imaging: To confirm whether the frequencies of fluctuations observed in MRI are consistent with fluctuating arterial or arteriolar diameters, we will co-register the MRI with optical imaging observed in the same animals over the same durations. In each image, we will identify up to 10 glomeruli with visible afferent arterioles in the optical image. We will measure arterial and arteriolar diameters (n=10 of each) in in each image and create a time course over 15 minutes. We will then co-register the optical and MR images based on the fiducial edge of the optical framework and compare the power spectrum of the time-courses from MRI and optical imaging, performing phase-corrected correlation between the two and using ANOVA with p<0.05 threshold to compare between groups of glomeruli (approximately 200 total) and MRI in voxels within and across animals. We expect strong correlation between MRI and optical measurements because manipulation of the TGF or vasogenic response causes up to 50% change in arteriolar diameter, visible with optical imaging. We do not expect that blood oxygenation will significantly affect the MRI signal in voxels containing glomeruli because most oxygen is extracted in other parts of the nephron, so the modulation of the MRI signal at the glomeruli should be specific to oscillations in vascular diameters.

Inhibition of autoregulation: We will examine the spectra in each voxel before and after furosemide, and compare to the healthy rats above. We expect that furosemide at the dose described above will eliminate signal power in the TGF band (primarily in cortex) and should significantly reduce power in the myogenic band. Resting state MRI data after inhibition of autoregulation will confirm that the resting state MRI signal in those bands is primarily associated with autoregulation, and allow us to quantify the effect of any blood oxygen contribution to the SE-EPI and GRE-EPI signals in medulla.

Spontaneously hypertensive rat (SHR): Histological slides will be scored for % vascular and interstitial fibrosis, as observed in our preliminary studies. We expect to observe a strong correlation between development of hypertension in the SHR model, histopathology scores of vascular fibrosis, and loss of myogenic power. We expect some decrease in the TGF response to this loss of myogenic regulation by 36 weeks, and potentially a shift in frequencies in the TGF band due to changes in local pressure during loss of the myogenic response.

Our preliminary studies have allowed us to gain experience with the typical problems of low frequency MRI, including physiological monitoring and stabilization and aliasing from higher frequency fluctuations into the bands of interest. A TR of 250 ms has been sufficient to eliminate aliasing into our bands of interest, but we may adjust TR if there are issues. Motion is always a concern in vivo, but our frequencies of interest are extremely low. Motion may be reduced by gating or changing the phase-encoding direction to be orthogonal to the direction of motion. If motion elimination by gating or position is not satisfactory, we will apply post-processing. If there are any issues with co-registration, we will perform high-resolution CFE-MRI in the excised, perfused, fixed kidney and co-register the in situ and externalized resting-state data. Low-dose isoflurane was successful in our preliminary studies. However, if we find limited reproducibility, we will test other approaches, such as low-dose medetomidine and isoflurane. If the furosemide does not significantly alter TGF or myogenic responses, we will consider the ureteric clamp or an ischemia reperfusion injury (IRI) model to remove both fluctuations. If the differences between any cohorts are not statistically significant, we may increase the number of animals to overcome natural variability in the spectra. We expect that we may perform whole-kidney 3D imaging using our current protocols. However, if we have insufficient signal to acquire in the required TR, we may apply sparse acquisition tools.

General Protocols

MRI: MRI will be performed at 9.4T Bruker scanner using volume coil as transmit and custom surface receiver coil. All animals will be anesthetized using a Ketamine-Xylazine cocktail. For imaging before externalization, rats will be maintained on anesthesia. For externalization, left kidney will be externalized and the animal transferred to MRI cradle. The externalized kidney will be fixed on a custom platform. $O_2$ and 1.5-2.25% isoflurane will be used to maintain respiration and core temperature by heating pad. ECG and pulse oximetry will be measured using SA instrument. SE-EPI: TR/TE=250 ms/13 ms, in-plane resolution=0.3 mm², slice thickness-0.5 mm, number of slices=15, number of averages=1, number of dummy scans=62, acquisition time of ~15 minutes. GRE-EPI: TR/TE-30 ms/10 ms, in-plane resolution=0.3 mm², slice thickness=0.5 mm, 3D acquisition, number of averages=1, number of dummy scans=62, total acquisition of ~15 minutes. T1-weighted scans for vessels are the same sequence with TR=50 ms.

GFR in SHR Model: Glomerular filtration rate (GFR) will be measured in each animal weekly using an elimination kinetic curve acquired from a transdermal device (MediBeacon, Mannheim, Germany) that detects FITC-labeled sinistrin in the blood. We will noninvasively monitor GFR monthly beginning at one month and ending at euthanasia.

Example 2

Figure 8:
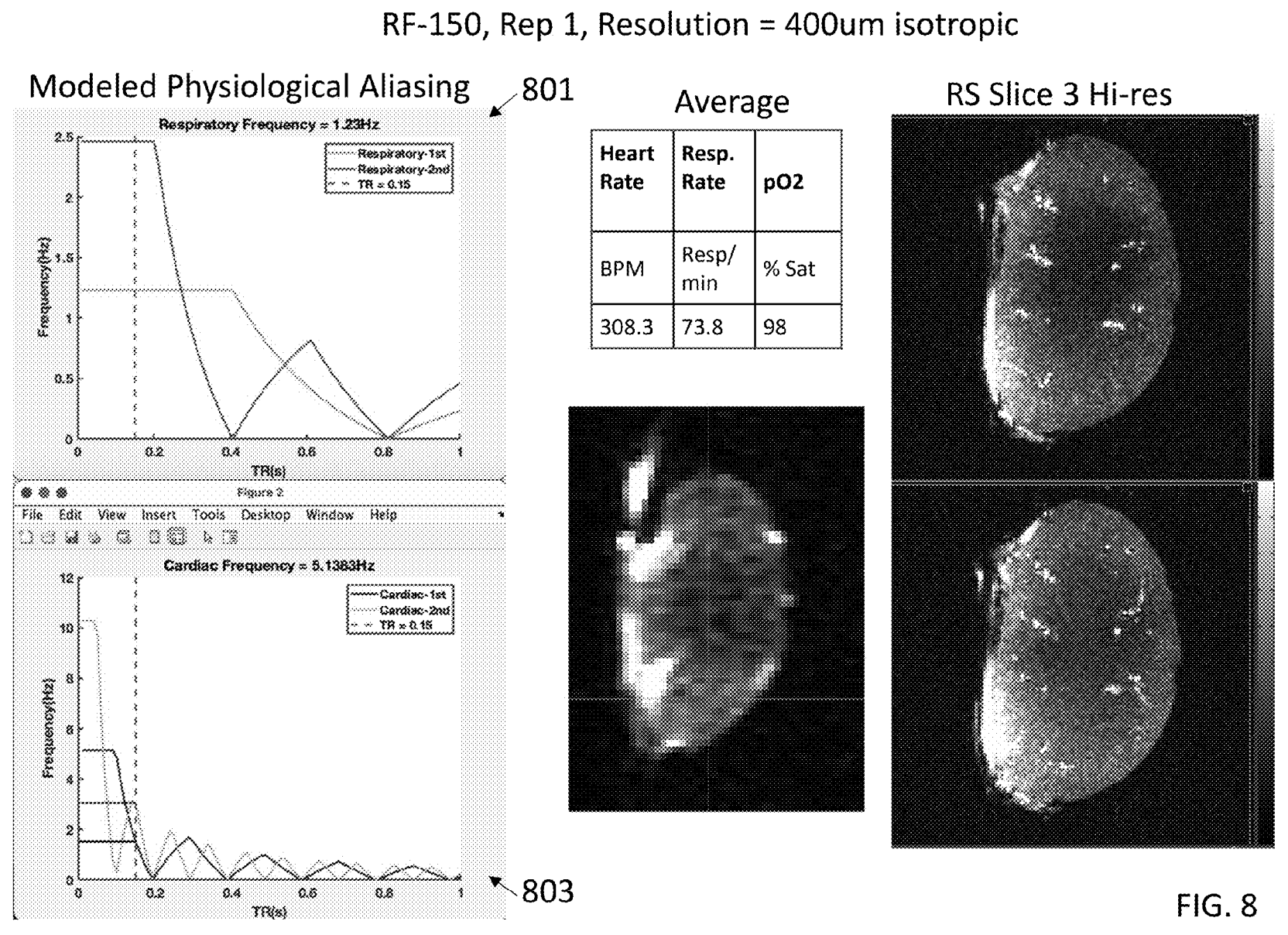

Physiological fluctuations that occur at a frequency higher than the Nyquist frequency of sampling (TR) are aliased into the power spectra, which may cause errors in the measured power spectra. To overcome errors caused by aliasing, we measure cardiac and respiratory signals continuously, and compute the aliased frequencies expected for up to three harmonics of these signals. We then confirm that our chosen TR is sufficient to avoid aliasing, or adjust TR to avoid it. FIG. 8 shows the effects of TR on the aliasing of respiratory and cardiac signals using an example TR of 150 ms. During scanning, the cardiac and respiratory signals were separately measured and high resolution images of the same anatomy as in the resting-state MRI were acquired for verification of the anatomy and locations of the voxels. Plots 801 and 803 show the effects of TR on aliasing of respiratory and cardiac signals, respectively. When TR is chosen at 150 ms, peaks of first and second respiratory harmonics (plot 801) and first and second cardiac harmonics (plot 803) are not aliased into the Nyquist frequency range corresponding to TR of 150 ms, reducing the aliasing errors.

Figure 9A:
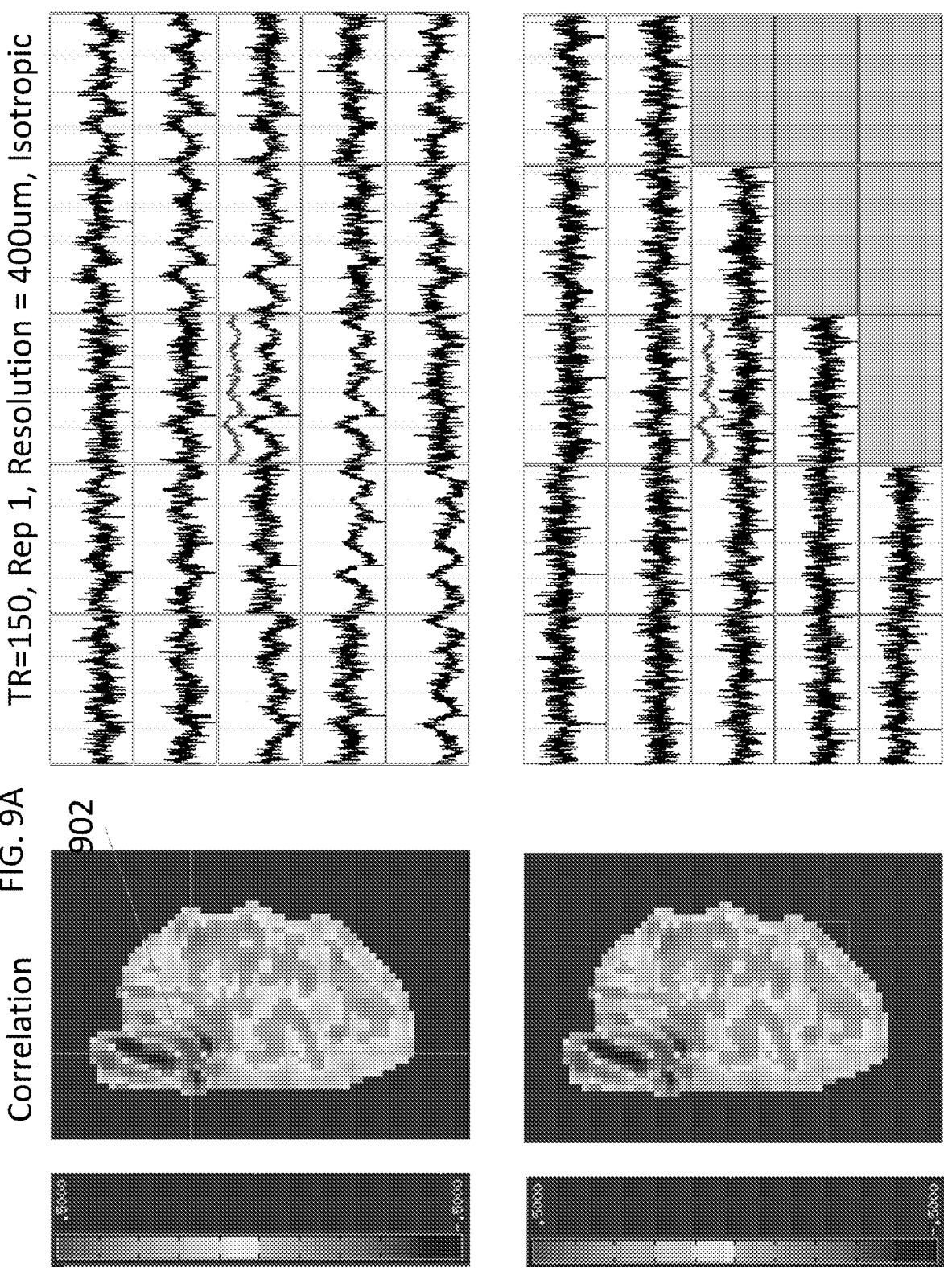
FIGS. 9A-9C show cross-correlations of times series.
Figure 9B:
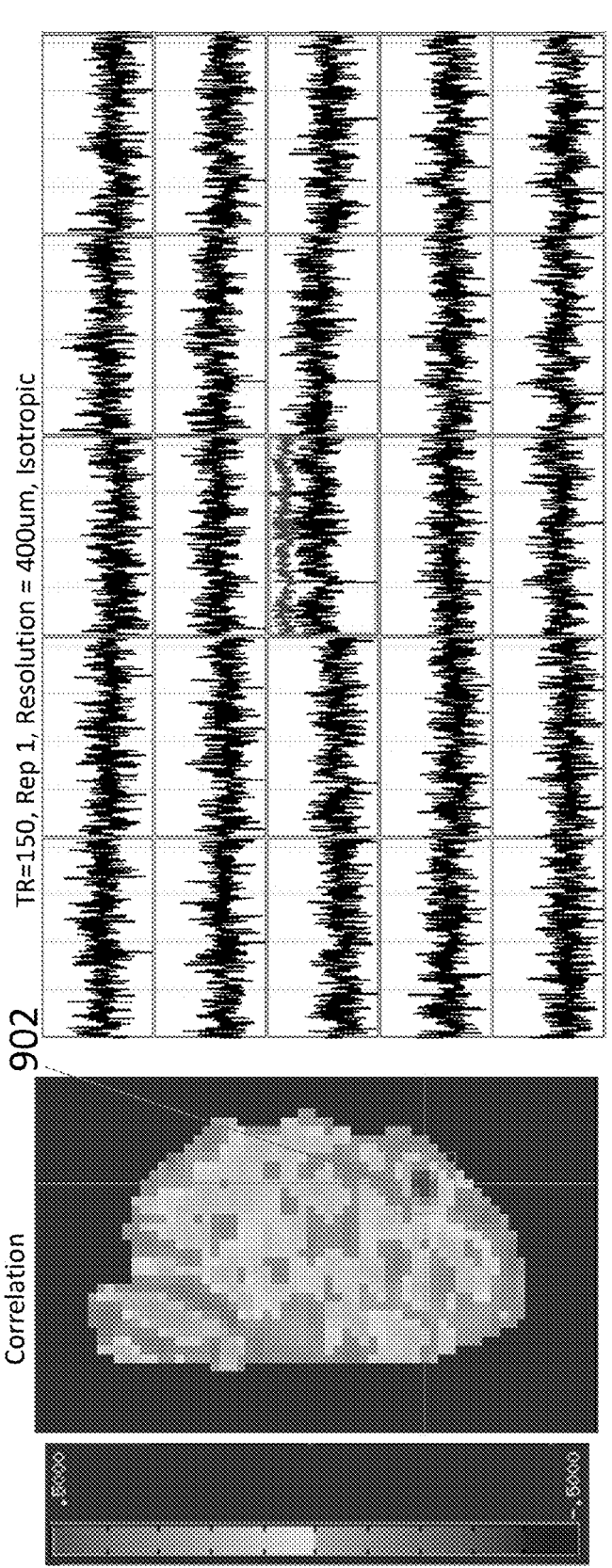
Figure 9C:
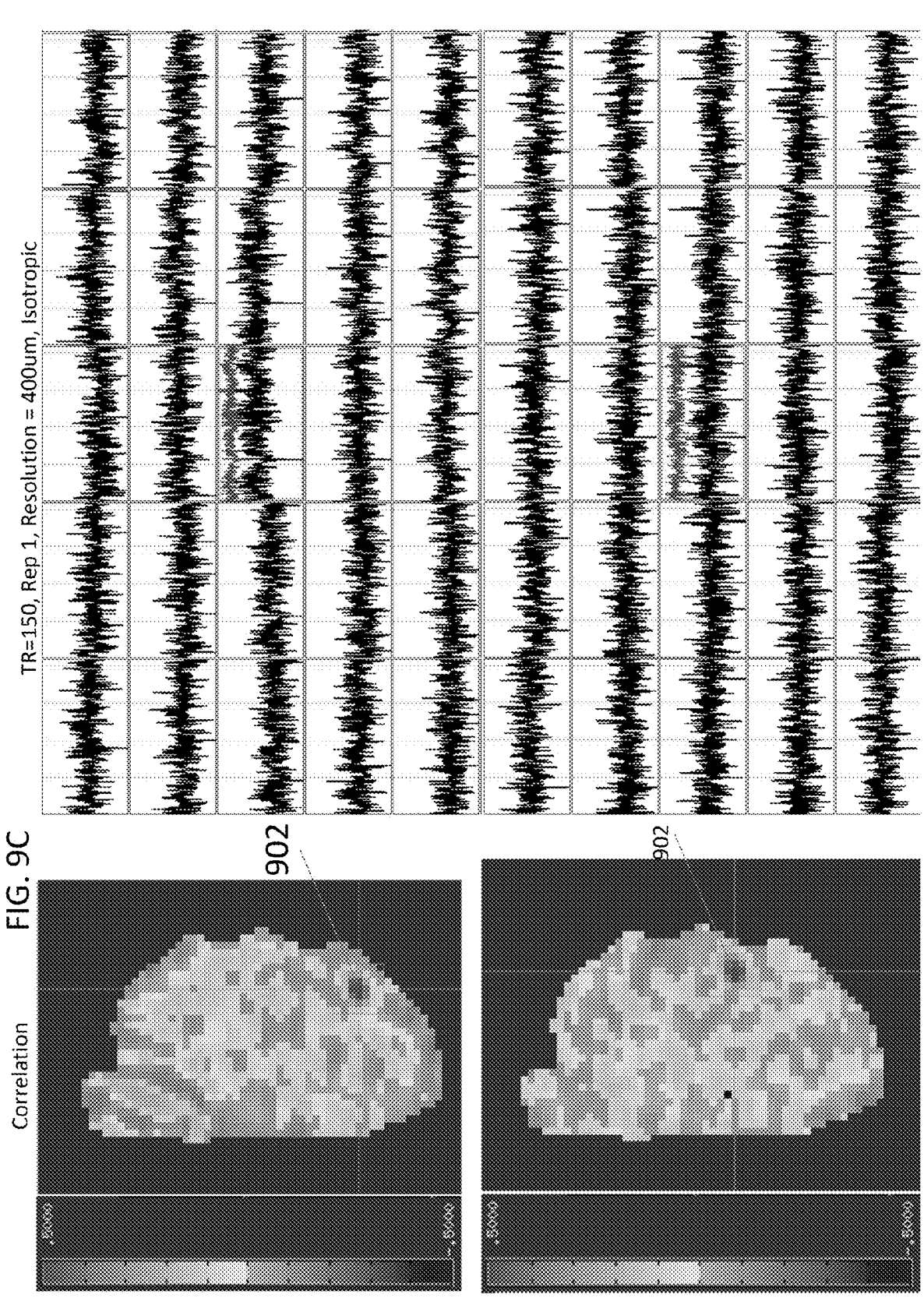
Figure 10A:
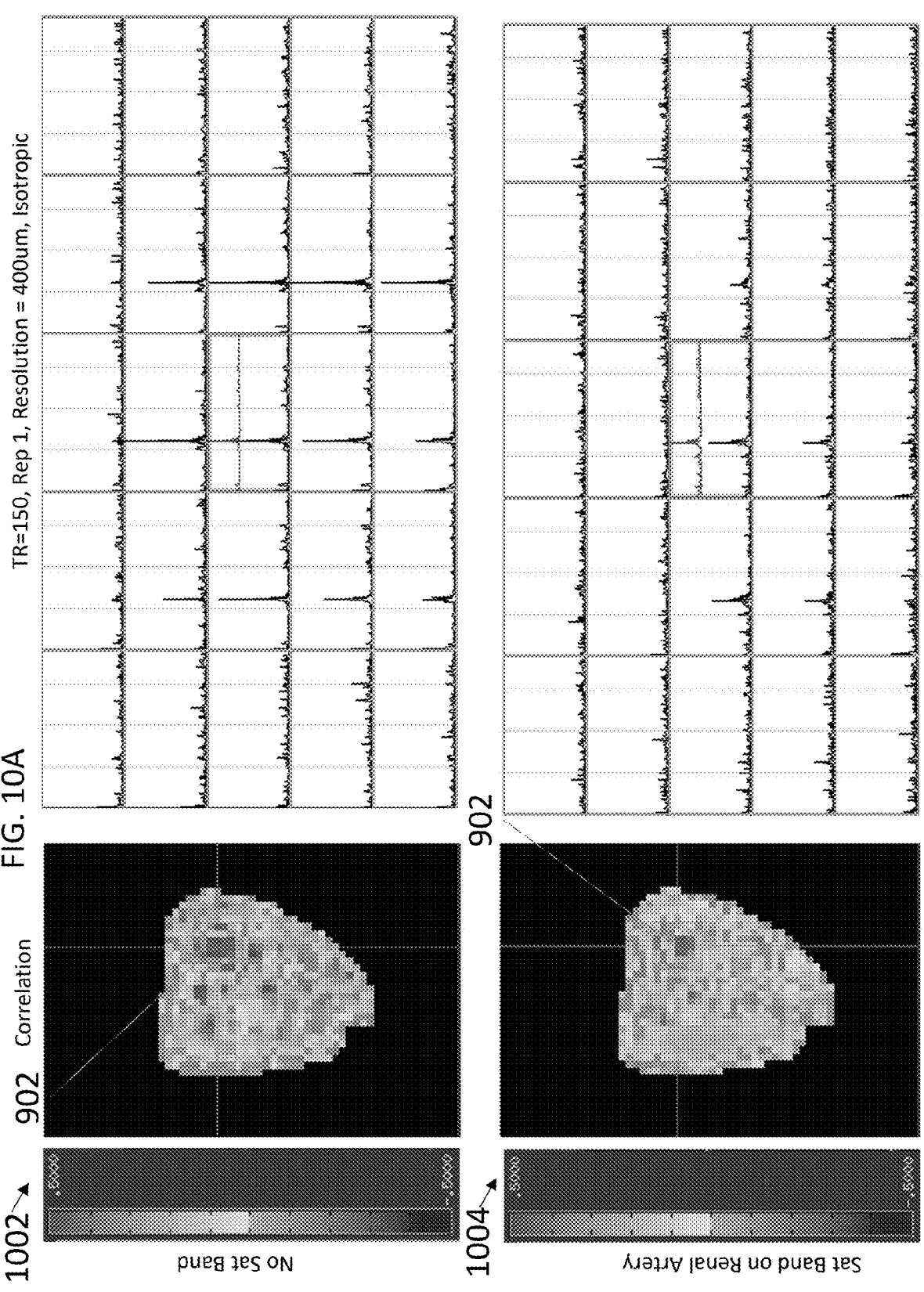
FIGS. 10A and 10B show cross-correlations of power spectra.
Figure 10B:
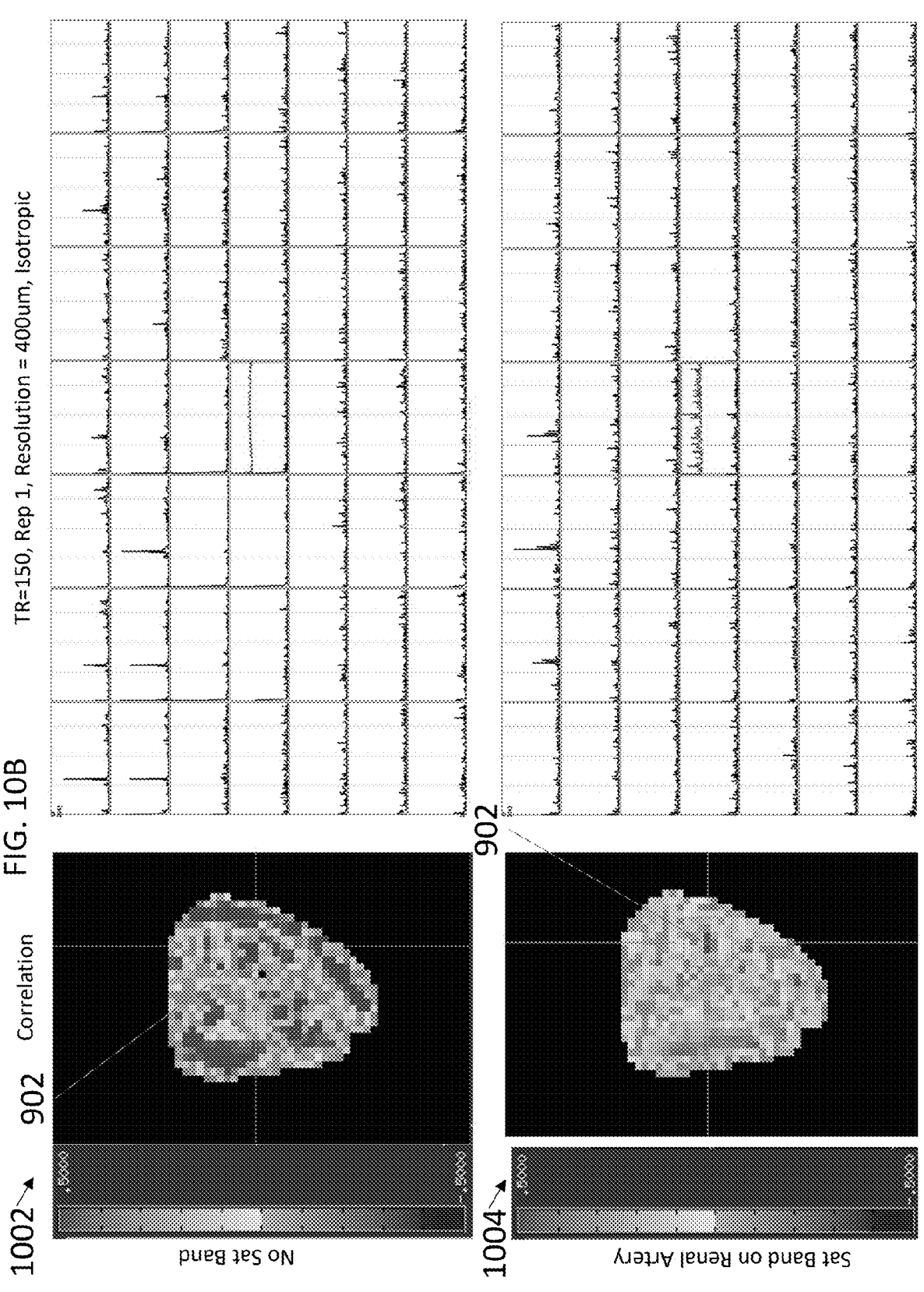

FIGS. 9A-10B show cross-correlations based on the data acquired with resting state MRI. TR is 150 ms. FIGS. 9A-9C are cross correlations of the time series at each voxel with a reference time series. The reference time series was chosen as the time series of a selected reference voxel 902. Because of phase changes in the time series, neighboring voxels have higher cross correlations than voxels farther away from reference voxel 902 (see maps of cross correlations). To minimize the effects from phases, we performed a correlation of the magnitude spectrum from each voxel with the spectrum from every other voxel (after linear detrending or any other filtering). FIGS. 10A and 10B show the cross correlation of the magnitude spectrum of each voxel with a reference power spectrum. The reference spectrum was chosen as selected reference voxel 902. We observed spatial patterns in the correlations between voxels. The spatial patterns likely indicate coordinated physiological fluctuations associated with either vascular or nephrovascular units. The phenomenon may indicate how nephrons and vessels work together across the kidney to maintain GFR, and the coupling is likely disrupted in disease. FIGS. 10A and 10B also show myogenic responses are relatively pronounced at and around vessels. Rows 1002 are data when a saturation band was not applied during resting state MRI. Rows 1004 are data when a saturation band was applied during resting sate MRI. A saturation band suppresses signals from flow, thereby reducing myogenic responses.

At least one technical effect of the systems and methods described herein includes (a) mapping autoregulation using resting state MRI; (b) identifying the TGF portion of autoregulation; (c) identifying a portion of autoregulation corresponding to myogenic responses; and (d) generating maps of autoregulation.

Example embodiments of systems and methods of autoregulation mapping are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of mapping autoregulation of a kidney using magnetic resonance (MR) imaging, comprising:
   acquiring a time series of MR images of a subject using a non-contrasted resting state MR imaging to detect physiological fluctuation slower than a respiratory rate of the subject by:
      acquiring the time series of MR images while the subject is at rest by:
         acquiring MR images of an imaging region repeatedly over a period of time by applying a pulse sequence,
      wherein the imaging region includes at least a kidney of the subject;
   analyzing the time series of MR images along a temporal dimension;

identifying features corresponding to autoregulation of the kidney including tubuloglomerular feedback (TGF) in voxels of the MR images based on the analysis;
generating a map and/or a metric of the autoregulation based on the identified features; and
outputting the map and/or the metric.

2. The method of claim 1, wherein analyzing the time series further comprises:
   for each voxel in the MR images,
      computing a power spectrum at the voxel based on a time series corresponding to the voxel.

3. The method of claim 1, wherein:
   analyzing the time series further comprises, for each voxel in the MR images, computing a cross correlation of a time series corresponding to the voxel with a reference time series; and
   identifying features further comprises identifying the features based on the computed cross correlations.

4. The method of claim 1, wherein:
   analyzing the time series further comprises:
      for each voxel in the MR images,
         computing a power spectrum at the voxel based on a time series corresponding to the voxel; and
         computing a cross correlation of the power spectrum at the voxel with a reference power spectrum; and
   identifying features further comprises identifying the features based on the computed cross correlations.

5. The method of claim 1, wherein acquiring a time series further comprises:
   applying a saturation band in acquiring the time series of MR images.

6. The method of claim 1, wherein acquiring a time series further comprises:
   acquiring respiratory signals and cardiac signals of the subject;
   determining a time of repetition (TR) in acquiring the time series of MR images based on the respiratory signals and the cardiac signals; and
   acquiring the time series of MR images using the determined TR.

7. The method claim 1, wherein acquiring a time series further comprises:
   acquiring the time series of MR images while the subject is at rest and passively receiving exogenous manipulation.

8. The method of claim 2, wherein identifying features further comprises:
   identifying features corresponding to the TGF based on a power spectrum in a TGF band.

9. The method of claim 2, wherein identifying features further comprises:
   identifying features corresponding to a myogenic response in the kidney based on a power spectrum in a myogenic band.

10. The method of claim 3, wherein the reference time series is a time series corresponding to a reference voxel.

11. The method of claim 4, wherein the reference power spectrum is a power spectrum corresponding to a reference voxel.

12. The method of claim 8, wherein the TGF band is in a range from 0 to 100 mHz.

13. The method of claim 9, wherein the myogenic band is in a range from 100 mHz to 300 mHz.

14. A method of mapping autoregulation of a kidney using magnetic resonance (MR) imaging, comprising:
   receiving a time series of MR images of a subject, wherein the time series of MR images were acquired using a non-contrasted resting state MR imaging to detect physiological fluctuation slower than a respiratory rate of the subject by:
   acquiring the time series of MR images while the subject is at rest by:
      acquiring MR images of an imaging region repeatedly over a period of time,
      wherein the imaging region includes at least a kidney of the subject;
analyzing the time series of MR images along a temporal dimension;
identifying features associated with autoregulation of the kidney in voxels of the MR images based on the analysis;
generating a map and/or a metric of the autoregulation based on the identified features; and
outputting the map and/or the metric.

15. The method of claim 14, wherein:
analyzing the time series further comprises:
   for each voxel in the MR images,
      computing a power spectrum at the voxel based on a time series corresponding to the voxel; and
identifying features further comprises:
   identifying features corresponding to a tubloglomerular feedback (TGF) based on a power spectrum in a TGF band.

16. The method of claim 14, wherein:
analyzing the time series further comprises:
   for each voxel in the MR images,
      computing a power spectrum at the voxel based on a time series corresponding to the voxel; and
identifying features further comprises:
   identifying features corresponding to a myogenic response in the kidney based on a power spectrum in a myogenic band.

17. The method of claim 14, wherein:
analyzing the time series further comprises, for each voxel in the MR images, computing a cross correlation of a time series corresponding to the voxel with a reference time series; and
identifying features further comprises identifying the features based on the computed cross correlations.

18. The method of claim 14, wherein:
analyzing the time series further comprises:
   for each voxel in the MR images,
      computing a power spectrum at the voxel based on a time series corresponding to the voxel; and
      computing a cross correlation of the power spectrum at the voxel with a reference power spectrum; and
identifying features further comprises identifying the features based on the computed cross correlations.

19. A method of mapping autoregulation of one or more organs outside a central nervous system of a subject using magnetic resonance (MR) imaging, comprising:
receiving a time series of MR images of a subject, wherein the time series of MR images were acquired using a non-contrasted resting state MR imaging to detect physiological fluctuation slower than a respiratory rate of the subject by:
   acquiring the time series of MR images while the subject is at rest by:
      acquiring MR images of an imaging region repeatedly over a period of time,
      wherein the imaging region includes one or more organs outside a central nervous system of the subject;
analyzing the time series of MR images along a temporal dimension;
identifying features associated with autoregulation of the one or more organs in voxels of the MR images based on the analysis;
generating a map and/or a metric of the autoregulation based on the identified features; and
outputting the map and/or the metric.

20. The method of claim 19, wherein:
receiving a time series of MR images further comprises:
   receiving the time series of MR images of the imaging region including a first organ and a second organ; and
analyzing the time series further comprises:
   determining interorgan correlation between the first organ and the second organ by analyzing a time series corresponding to a voxel in the first organ and a time series corresponding to a voxel in the second organ.

\* \* \* \* \*